United States Patent
Masson et al.

(10) Patent No.: US 8,244,555 B2
(45) Date of Patent: Aug. 14, 2012

(54) RULE MODEL FOR HEALTHCARE INFORMATION

(75) Inventors: Arnaud Masson, Nancy (FR); Romain Demoustier, Nice (FR)

(73) Assignee: Merge eClinical, Inc., Hartland, WI (US)

(*) Notice: Subject to any disclaimer, the term of this patent is extended or adjusted under 35 U.S.C. 154(b) by 734 days.

(21) Appl. No.: 12/160,479

(22) PCT Filed: Jul. 17, 2006
(Under 37 CFR 1.47)

(86) PCT No.: PCT/IB2006/003157
§ 371 (c)(1),
(2), (4) Date: Jan. 12, 2009

(87) PCT Pub. No.: WO2008/010013
PCT Pub. Date: Jan. 24, 2008

(65) Prior Publication Data
US 2009/0248604 A1    Oct. 1, 2009

(51) Int. Cl.
*G06Q 10/00* (2012.01)

(52) U.S. Cl. .......................................................... 705/2

(58) Field of Classification Search ................ 705/2, 3, 705/4
See application file for complete search history.

(56) References Cited

U.S. PATENT DOCUMENTS

| | | | |
|---|---|---|---|
| 7,487,134 B2* | 2/2009 | Grichnik et al. | 706/60 |
| 7,627,491 B2* | 12/2009 | Feyen et al. | 705/4 |
| 2004/0122703 A1* | 6/2004 | Walker et al. | 705/2 |
| 2005/0010451 A1* | 1/2005 | Marks et al. | 705/3 |

OTHER PUBLICATIONS

International Bureau of WIPO, International Preliminary Report on Patentability for International Application No. PCT/IB2006/003157, dated Jan. 20, 2009, 1 page.

Written Opinion of the International Searching Authority for International Application No. PCT/IB2006/003157, dated Jan. 20, 2009, 8 pages.

* cited by examiner

*Primary Examiner* — Vivek Koppikar
*Assistant Examiner* — Edward Winston, III
(74) *Attorney, Agent, or Firm* — Michael Best & Friedrich LLP

(57) ABSTRACT

Healthcare information data is managed by, on a computer, maintaining a model of a state of a system based on the healthcare information, receiving a transaction representing a change to the system, determining that the change complies with a rule, and changing the model according to the transaction.

27 Claims, 7 Drawing Sheets

RULE MODEL FOR HEALTHCARE INFORMATION

TECHNICAL FIELD

This disclosure relates to a rule model for healthcare information.

BACKGROUND

Healthcare information must be accessed by developers, researchers, health care professionals, vendors, managers, insurers, and regulators, among others. The people accessing the information may have a diverse set of needs and resources and be distributed over a large geographic area. Numerous data systems may be required to interact to maintain all the required information and deliver it to the correct places at the proper times.

For managing healthcare information, current approaches include electronic data capture, large-scale databases of records, and automated systems to maintain and report the progress of the study. For compatibility between users and to comply with government requirements, such as for electronic reporting of clinical data to the FDA, extensible standards such as the Clinical Data Interchange Standards Consortium (CDISC) Operational Data Modeling (ODM) standard are used to store and model clinical data. These standards allow vendors to extend the capability of a standard model to include additional information or functionality of value to the vendor's customers. The FDA requires access to such files, and their auditing benefits from the traceability and retrieval that such standards enable.

Projects in various healthcare areas have such data tracking & reporting requirements, including clinical studies, complaints about healthcare products, treatments, or drugs, managing patient records, etc. Problems may arise when different aspects of a project use incompatible data systems and information fails to be exchanged in an efficient manner, or at all, for example if a patient sees several specialists who all use different record-keeping systems. Patient records are collected by physicians and experts to keep track of the medical activity and status of a patient, and typically require the tracking of thousands of diverse pieces of information. Clinical trials to determine the safety and efficacy of new drugs, treatments or medical devices also typically require the tracking of such information, including not only patient records, but also experimental results, progress reports, and financial information. Complaints concerning healthcare products must be closely monitored and rapidly reported and addressed. Timeliness and completeness of a manufacturer's response to such complaints, and records about that response, is critical.

As used in this application, the term "healthcare information" refers to the results or data produced by or associated with any analysis, research, or data collection aimed at evaluating, reporting or claiming information that impacts the health state of a person. "Clinical trial" refers to any study, research, trial, or investigation of the medical efficacy or safety of a medical substance or device. "Patient records" refers to the results or data produced by or associated with any analysis, research, or data collection aimed at the current or past state of a patient in regards to the medical treatments or procedure he has been subject to.

SUMMARY

In general, in one aspect, healthcare information data is managed by, on a computer, maintaining a model of a state of a system based on the healthcare information, receiving a transaction representing a change to the system, determining that the change complies with a rule, and changing the model according to the transaction.

Implementations may include one or more of the following features.

Changing the model includes adding the rule to a set of rules in the model. Maintaining the model includes for each transaction in a set of transactions, if the transaction alters data in the system, altering corresponding data in the model, and if the transaction alters a rule in the system, altering a corresponding rule in the model.

The change complies with the rule if the transaction changes data in the system and, if the corresponding data in the model is changed, the data in the model will meet a condition defined by the rule. Determining that the change complies with the rule includes evaluating what the state of data in the model will be if the change identified by the transaction is made, and determining that the state of the data will satisfy the condition defined by the rule.

The change complies with the rule if the transaction changes the rule and data in the model meets a condition defined by the changed rule. Determining that the change complies with the rule includes evaluating the state of data in the model, and determining that the state of the data will satisfy the condition defined by the rule.

The rule includes an identification of a type of alteration to the state of the system, and a condition, and determining that the change complies with the rule includes determining that the transaction represents an alteration to the state of the system matching the type identified by the rule, and determining whether the condition in the rule is satisfied.

The condition includes a relationship between a user submitting the transaction and a set of users. The relationship is that the user is a member of the set of users. The relationship is that the user is a member of a first set of users, and the relationship is satisfied if the user is a member of a second set of users that is related to the first set of users. The condition includes a relationship between two or more of: a value of an element in the model, a value of an item of data external to the model, a value of an element in the transaction, a result of a computation determining that the change complies with a rule includes evaluating an expression. The expression includes sub-expressions, and evaluating the expression includes evaluating each of the sub-expressions to produce results, and evaluating the expression based on the results. The expression includes a definition of a data item, and evaluating the expression includes constructing the data item according to the definition.

The model includes a hierarchy of elements, the rule is associated with a first element in the hierarchy, and determining that the change complies with the rule includes determining that a second element is subordinate to the first element and evaluating the value of the second element. The second element is a child of the first element. The model includes a hierarchy of elements, the rule is associated with a first element in the hierarchy, and determining that the change complies with the rule includes evaluating values of a second and third element that are each subordinate to the first element but not to each other. At least one of the second and third elements is a child of the first element.

Aspects may include a method, a computer or computer system for carrying out the method, software for configuring a computer to carry out the method, and other embodiments.

Advantages include increased reliability of modeled data. Rules and data can both be added to the model. New rules and data are evaluated against existing rules data. Problems are identified before the model is permanently updated. Rules and related properties can be inherited. Rules can be hard-coded in the software or may be configured by users.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Data Model

One way to manage a diverse amount of healthcare information data is a data model. A data model consists of a set of elements and associated values. For example, the elements of a model may include clinical trial data such as protocol definitions, users, roles, experimental results, etc. Depending on the size and complexity of the study, the elements used in the data model to represent the components of the study may be very complex themselves, including files, databases, or even additional data models. The elements could be arranged in a flat structure, in a hierarchy, or in some other arrangement. Similar models can be used to manage patient records or complaints about healthcare products.

Figure 1:
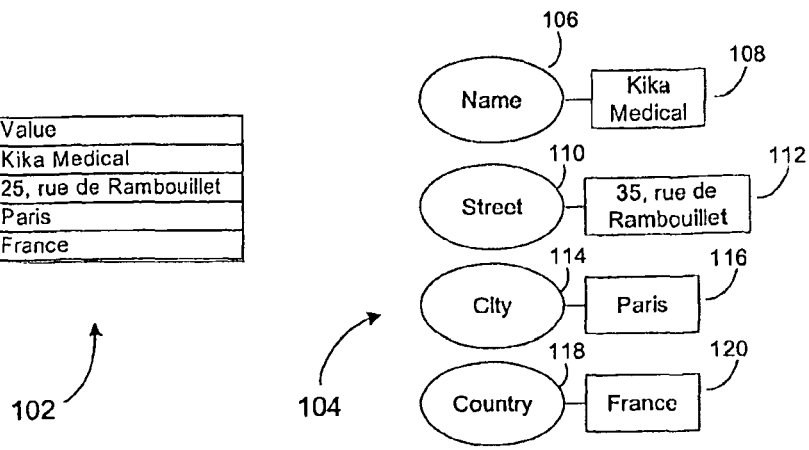
FIG. 1 is an example of model data expressed in tabular form and a corresponding block diagram.
Figure 2:
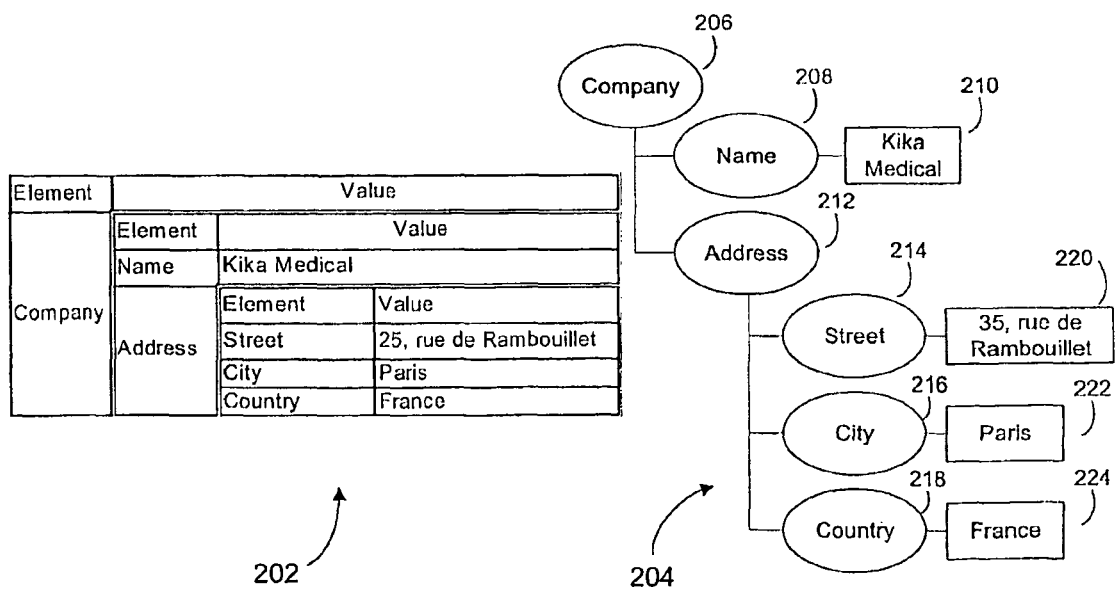
FIG. 2 is an example of the model data and diagram of FIG. 1 to which hierarchical relationships have been added.

There are numerous ways the data comprising the value of an element may be represented. For example, as shown in FIG. 1, values may be associated with elements in Java objects, illustrated in table form in table 102. An element that has a value associated with it is represented in an object. In the Java object represented by table 102, element "Name" has value "Kika Medical". Other elements and associated values represent an address. In the corresponding block diagram 104 of the same data, elements are represented by ovals 106, 110, 114, and 118, while data values are represented by rectangles 108, 112, 116, 120. In a hierarchical data model, as shown in FIG. 2, one element in an object may have as its value additional elements, which in turn may have values or contain still additional elements. For example, an object represented by table 202 corresponds to a hierarchical data model 204, in which the element "Company" 206 has as its value sub-elements "Name" 208 and "Address" 212. The sub-element "Name" has value "Kika Medical" 210 while the sub element "Address" has additional sub-elements 214, 216, and 218 corresponding to the parts of the address, each with appropriate values 220, 222, 224. In some cases, the value of an element may be represented by binary data, for example, a digital image. Possible implementations of such a feature are discussed below. Other data formats can be used, such as comma-separated value files, spreadsheets, or databases. The elements and values of the data model could similarly be represented by XML tags or other data formats.

A data model can be very complex, containing a large amount of information. As a clinical study advances or a patient receives ongoing medical care, the data model is continually updated so that it always represents the current status of all aspects of the subject matter. Whenever new information is available, it is added to the data model. If a user needs current information about some aspect of the modeled information, they use a client to access the model and find the current state of the relevant data. For example, when new information concerning a patient is available, a doctor will add those results to the model. If the doctor needs to see the patient's records, he uses a client to access the model and retrieve those records.

In some examples, the data model is an extension of the Clinical Data Interchange Standards Consortium (CDISC) Operational Data Modeling (ODM) standard, which documents a hierarchical structure of clinical data elements. One part of each ODM file, known as the metadata, describes the data collected in a study. The metadata consists of definitions, with one type of definition for each of five data levels:

|   | Data Level | Definition Type |
|---|---|---|
| 1 | SubjectData | Protocol |
| 2 | StudyEventData | StudyEventDef |
| 3 | FormData | FormDef |
| 4 | ItemGroupData | ItemGroupDef |
| 5 | ItemData | ItemDef |

The first four levels are container levels while the last level is for actual data values. Container definitions are lists of references, which are pointers to other data definitions. For example, the metadata defining an ItemGroupData-level element Demographics may contain references to ItemDefs Birth_Date and Patient_Sex, indicating that the Demographics element contains two sub-elements at the ItemData level, and these sub-elements are defined according to the Birth_Date and Patient_Sex item definitions and will contain the corresponding data. The item definitions at the ItemData level describe the type of data stored in the defined element, such as text, integer, float, date, etc. In the preceding example, the item definition Birth_Date would indicate that the value must be of type "date."

The CDISC standard defines two important elements, Repeating and Mandatory. Repeating, applicable to definitions, indicates whether an element can be included more than once. For example, a StudyEvent-level element Adverse_Event, defined by a StudyEventDef definition, may be repeated several times in a study, so the definition of Adverse_Event would include the element Repeating with a value "true." Mandatory is applicable to references and indicates whether a referenced sub-element is mandatory.

Transactions

The contents of a data model are changed by a transaction. A transaction may consist of instructions to add or remove elements, change the values of elements, or change the relationships between elements, such as their arrangement in a hierarchy. A single transaction may contain instructions to make multiple changes to the data model. For example, a transaction may instruct the data model to change the "Name" element of a particular person and add a "Telephone" element for that person. A transaction can be a data structure consisting of a subset of the elements of the data model it is intended to change. The values of the elements in the transaction could indicate explicit instructions, such as to add or delete an element. Alternatively, the values of the elements in the transaction could differ from the values already associated with the elements in the data model, such that the differences constitute instructions to change the values in the model accordingly.

Figure 3:
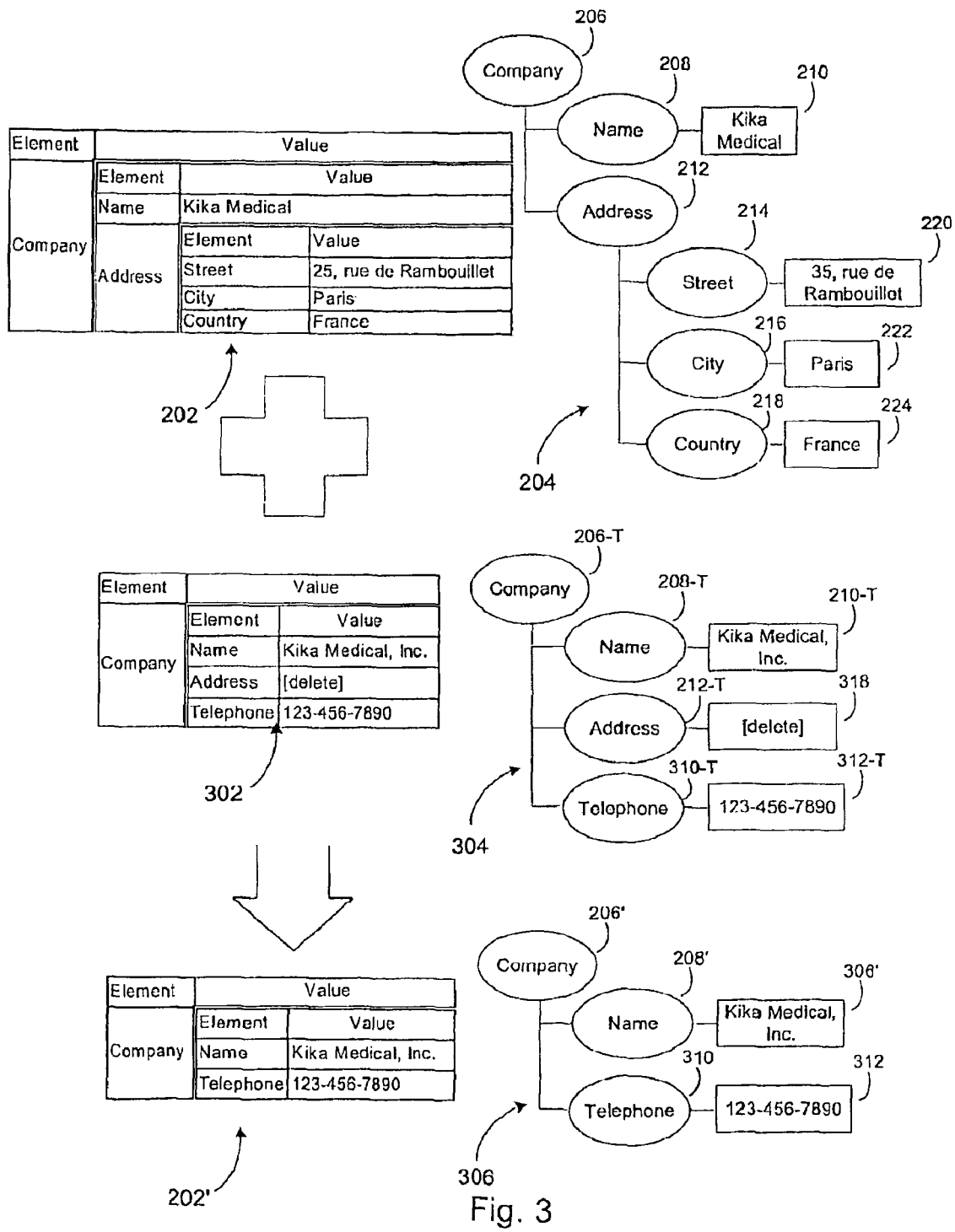
FIG. 3 is a flow diagram of illustrating a transaction starting with the model data table/diagram of FIG. 2 and making changes specified in a second model data table/diagram resulting in a third model data table/diagram.

A transaction may be represented in the same format as the data model itself. In some examples, as shown in FIG. 3, a transaction is represented by a Java object as illustrated in table 302 and the data model is stored in memory is a comparable format. Block diagrams 204, 304, and 306 illustrate the transaction and data model abstractly. A transaction consists of a set of elements in the object of table 302 corresponding to the object 202 representing the data model. The "Name" element 208-T has a different value 210-T than the corresponding element in the data model, so the transaction is regarded as an instruction to change the value of the "Name" element 208 in the data model. The "Address" element 212-T has a value consisting of the command "[delete]" 318, so the "Address" element 212 will be removed from the data model by deleting the corresponding element from the Java object. The "Telephone" element 310-T and its value 312-T are not found in the existing data model, so a new element and its value 312 will be added to the Java object. These changes are applied to the data model represented by the Java object illustrated in table 202 to produce an updated Java object, illustrated in table 202', with updated "Company" and "Name" elements 206' and 208', a new value 306' for the name element 208', and new "Telephone" element 310 having value 312.

In some examples, a minimum set of elements and corresponding values must be included in every transaction. Such elements may include a global unique identifier (GUID) (assigned by a system that processes the transactions), the date of the transaction, the user ID of the author of the modification, a reason for the modification, the GUID of the previous transaction, and references to binaries, if any. A transaction may implicitly indicate when data is to be added or changed, simply by including the new data, or it may be required in a particular implementation to explicitly indicate for each element referenced whether data is being added, changed, or deleted.

Implementation of the Model

Figure 4:
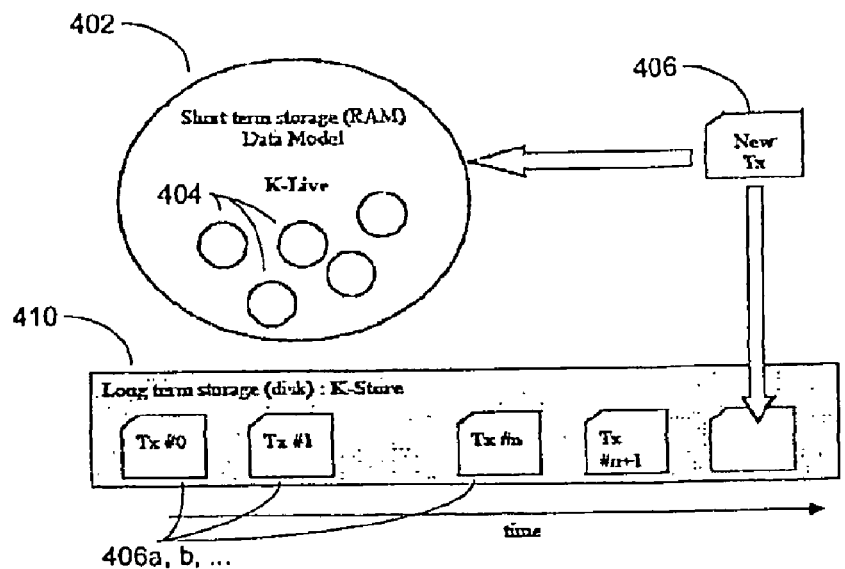
FIG. 4 is a block diagram of the input of a transaction simultaneously into a data model and into a long-term storage.

Two different components are used to store the data model in a complementary manner, as shown in FIG. 4. The short term storage 402 runs as an application on a computer system and maintains a representation of the current state of the data model. The model 404 consists of data in memory representing each element and its current value. By applying the instructions of each transaction to the data model currently in memory as the instructions are received, the representation of the model in the short term storage always represents the current state of the data model as of the most recent transaction, and can be quickly accessed to determine what that state is. When a new transaction 406 is received, the short term storage 402 analyses the transaction to determine what changes are to be made to the data model, and it makes those changes to the representation of the model 404 currently in memory. The short term storage may be limited for technical or other reasons. For example, if the data representing the current state of the data model is stored in volatile memory, that data will be lost if the computer hosting it is shut down. Storing the data in volatile memory may have advantages, such as allowing faster access to current information about the state of the data model to users or other processes that may require such information. The data representing the model could also be stored in a non-volatile memory, such as a hard disk or flash memory, with advantages and disadvantages corresponding to elements of the technology used.

The long term storage component 410 also runs on a computer system, which may be the same system as the one running the short term storage 402, or may be separate. It stores each new transaction 406 as it is received, without analyzing the transaction or applying it to the data model. Transactions are associated with a sequence value indicating the order in which they were received. A sequence of transactions 406a, b, etc. is referred to as a "series." When it is desired to reconstruct the current state of the data model, for example, after the server hosting the short term storage has been rebooted, this is done by starting with an empty model, containing no elements or a default set of elements, and then loading a series of transactions from storage and applying them to the data model according to their sequence numbers to reproduce the process that led to the present state of the data model. Because conditions external to the data model may change between the time a transaction is stored and the time it is used to recreate a change to the data model, it is desirable that the data values in a transaction contain actual values, rather than references to external parameters. For example, if an element is to have a value representing the date on which it was stored, the corresponding value in the transaction needs to represent the actual date, i.e., "1 Jan. 2006," not a pointer to that value in a computer system, for example, the system clock, which may change, even though such a pointer would have been sufficient on the day the transaction was stored.

Model Controller

Figure 5:
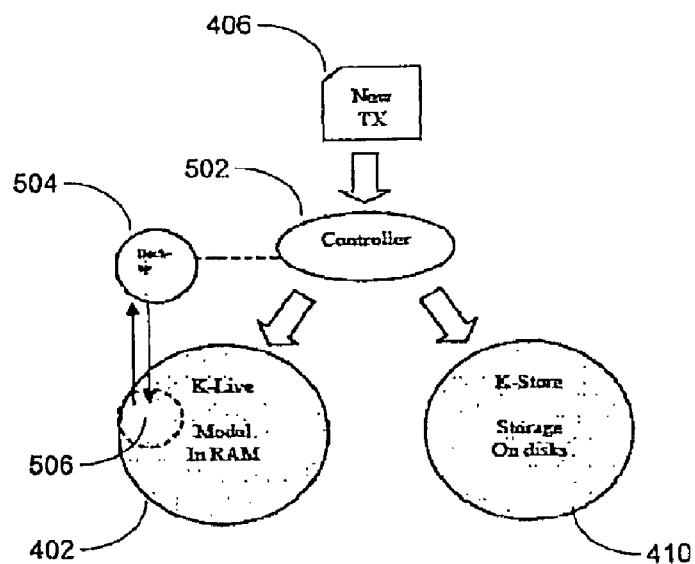
FIG. 5 is a block diagram of a controller handling the flow of a transaction to the components shown in FIG. 4.

As shown in FIG. 5, a controller module is another software application, and is configured to manage the flow of transactions from clients that access the data model. It may or may not operate on the same computer system as the other components. When a transaction 406 is received, a controller 502 checks it against a set of rules to confirm that the changes it instructs to the data model are valid. The controller then provides the transaction to both the short term storage 402 and the long term storage 410 for appropriate handling. To insure reliability, the controller analyses the changes that will be made by the transaction and makes a backup copy 504 of the part 506 of the data model, as represented in the current state, that is about to be modified by the transaction. The controller may be configured to backup a larger part of the data model than will clearly be affected by the changes, to assure that the backup is adequate. The transaction is then applied to the model by the short term storage 402, generating a new revision and current state. The state may then be checked against a set of rules to assure that the revised data model continues to comply with them. If a rule is violated, the transaction is rejected and the backup is used to restore the data model to the state that existed before the revision. If no rule is violated, then the controller 502 instructs the long term storage 410 to store the transaction. If for some reason the storage of the transaction is not successful, then the backup 504 is again used to restore the data model to its previous state. Even though no rules were violated by the changes, since they were not stored, the revised state will not be recreated when the sequence of transactions is again applied, so the current state should not reflect the new changes.

Rules

The rules used to accept or reject a new transaction can by divided into two categories. One is hard-coded rules, which are written into the programming of the server application, and not modifiable by any user. The other category is configured rules, which are specified by some privileged user at runtime, for example, with an application for managing the model. Hard-coded rules are used for immutable, low-level validations. For example, basic rules about clinical data include: "User can add a new Form only if the referenced Study Event exists," and "The OID of any data element must match the OID of a metadata Definition," and would typically be hard-coded.

Configured rules represent high-level validations, and are sometimes referred to as "business rules." They may be different between studies, and ordinary users may be able to define them. In some examples, the configured rules for a clinical study model only concern clinical data (the substantive part of the study model), while rules for modifications of users, roles, and metadata are hard-coded in the application code. In other examples, such rules could be configured rules modifiable while the study is underway. Only configured rules are discussed in the remainder of this disclosure.

Figure 6:
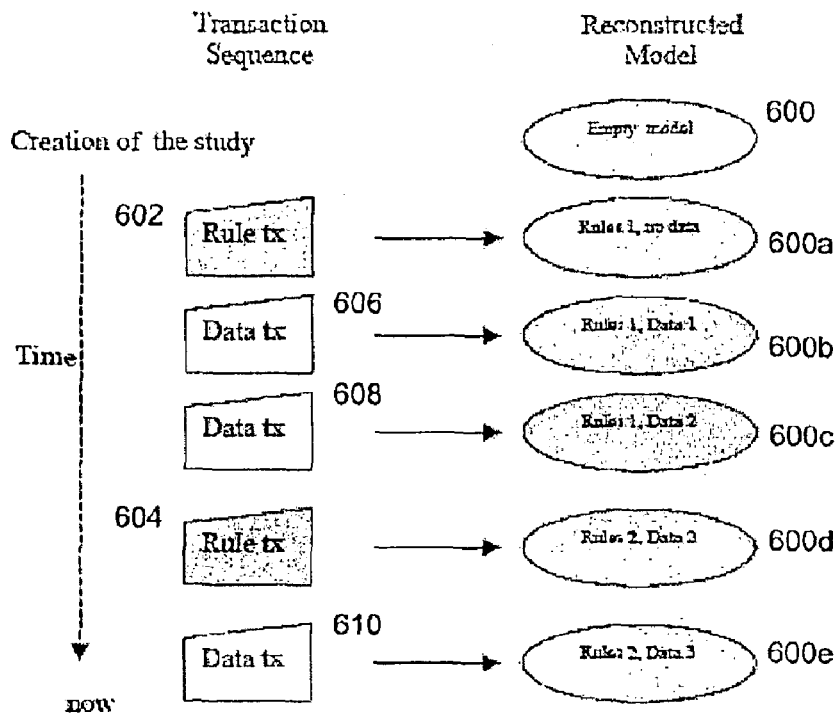
FIG. 6 is a block diagram of the addition of data and rules to a model like that of FIG. 1.

In one example, as shown in FIG. 6, configured rules 602, 604 are stored in the model 600 itself, and are managed the same way as other data in the model, for example, data added by transactions 606, 608, 610. Each addition of a rule or data results in a new state 600a-600e of the model 600. When the model controller rebuilds a previous state of the data, it also rebuilds the set of rules that were active at the same time.

Imperative vs. Declarative Rules

In the example of a Clinical Study, one possible approach is to configure the system with imperative rules of the form:

"If [Event] occurs, then the user can do [Action]"

In the example of a clinical study, a rule of this type may be:

"If the user adds the StudyEvent SCREENING, then the user can enter the StudyEvent FOLLOWUP" or "If the current date reaches Dec. 1, 2005, then the user can enter the StudyEvent FOLLOWUP"

Such imperative rules are evaluated after specific events, such as user actions, and trigger the execution of code that decides what actions users are capable of performing after the modification of the model.

Imperative rules are intuitive but may not provide a robust solution. In some examples, special flags must be attached to data elements to remember workflow decisions. This additional state must be consistent with the rest of the model and it may be difficult to maintain because a rule can have many dependencies and many rules can apply to the same action.

An alternative approach is to write declarative rules of the form:

"The user can do [Action] only if [Condition]"

In the example of a clinical study, a rule of this type may be:

"The user can add a FOLLOWUP only if the SCREENING exists and the current date is after Dec. 1, 2005"

Declarative rules can be evaluated "on-demand" before an action is performed to know if it is allowed. No special state has to be stored to remember the consequences of previous actions, though results of complex or frequent evaluations could be retained in accessible memory or storage. Such retained results would only be a cache, not a primary storage. Evaluation of declarative rules depends on the current model and determines what users are able to do with the model.

Declarative rules can be further divided into two categories, permissions and integrity conditions, discussed below. In addition, rules can be hard or soft. Soft rules can be referenced from hard rules, but they don't change the evaluation of transactions directly. A soft rule may be useful if two or more hard rules have a common sub-expression. Soft rules may also be used to display informational warnings to the user that don't actually indicate a transaction was rejected. Only hard rules are relevant to the remainder of this disclosure.

Rules are not checked again during the model reconstruction when the server starts-up, as detailed in the above-referenced application. Since the transactions were fully validated when they were stored, such verification is not required when they are subsequently re-applied to a reconstructed data model.

Permissions

Permissions specify which types of modification are allowed on a target element. Permissions are checked when the elements of a transaction are about to be applied to a sub-hierarchy of the target model. A permission is attached to an element, and includes a dynamic expression returning a Boolean, a set of operations to which the permission applies, e.g., Insert, Update, and Delete, and an ID. The dynamic expression is evaluated on the model state before any modification is made. The ID of a permission is locally unique to the definition of the element.

Figure 7:
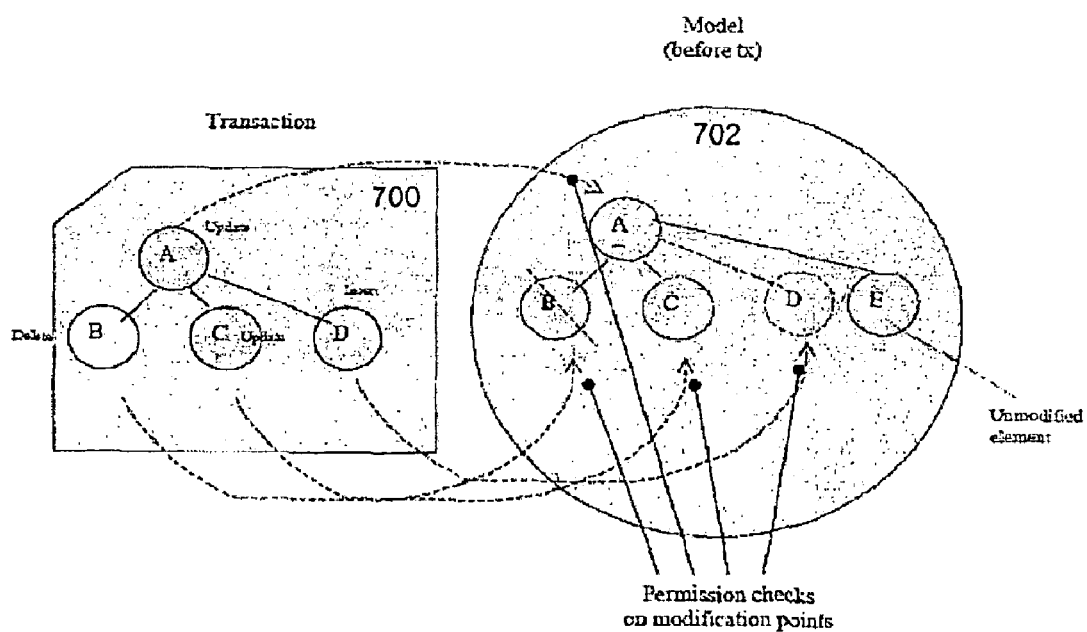
FIG. 7 is a block diagram of the application of rules to a transaction like that shown in FIG. 3.

In the example shown in FIG. 7, a transaction 700 makes several changes to the data in a model 702. It updates the values of elements A and C, inserts an element D, and deletes an element B. To make these changes, the permissions that will be checked are:

Permissions on element A applicable to update operations
Permissions on element B applicable to delete operations
Permissions on element C applicable to update operations
Permissions on element D applicable to insert operations If no permission is found for a given modification point, then the modification is accepted. Several permissions can be found for a given modification. In such a case, the individual evaluation results are grouped with an implicit AND operator. If at least one of the element modifications of the transaction is rejected by a permission, then the whole transaction is rejected.

The dynamic expression of a permission can use the hierarchical data in the current model (in the state as it was immediately before the transaction), the date and time of the transaction (fixed at the beginning of the validation process), or the roles given to the user that has initiated the transaction (also stored in the data model).

Integrity Conditions

Integrity conditions are rules that continuously check the consistency of the model. The integrity conditions of an element are evaluated only if the corresponding data has already been added (see "target path" below). No integrity condition may be false during the life of the model. In a typical implementation, integrity conditions only need to be checked after each attempt to modify the model. A consequence of this requirement is that not only must any data modification be rejected if it is not allowed by the rules associated with the relevant element, but also any rule modification must be rejected if it makes current data invalid.

Figure 8:
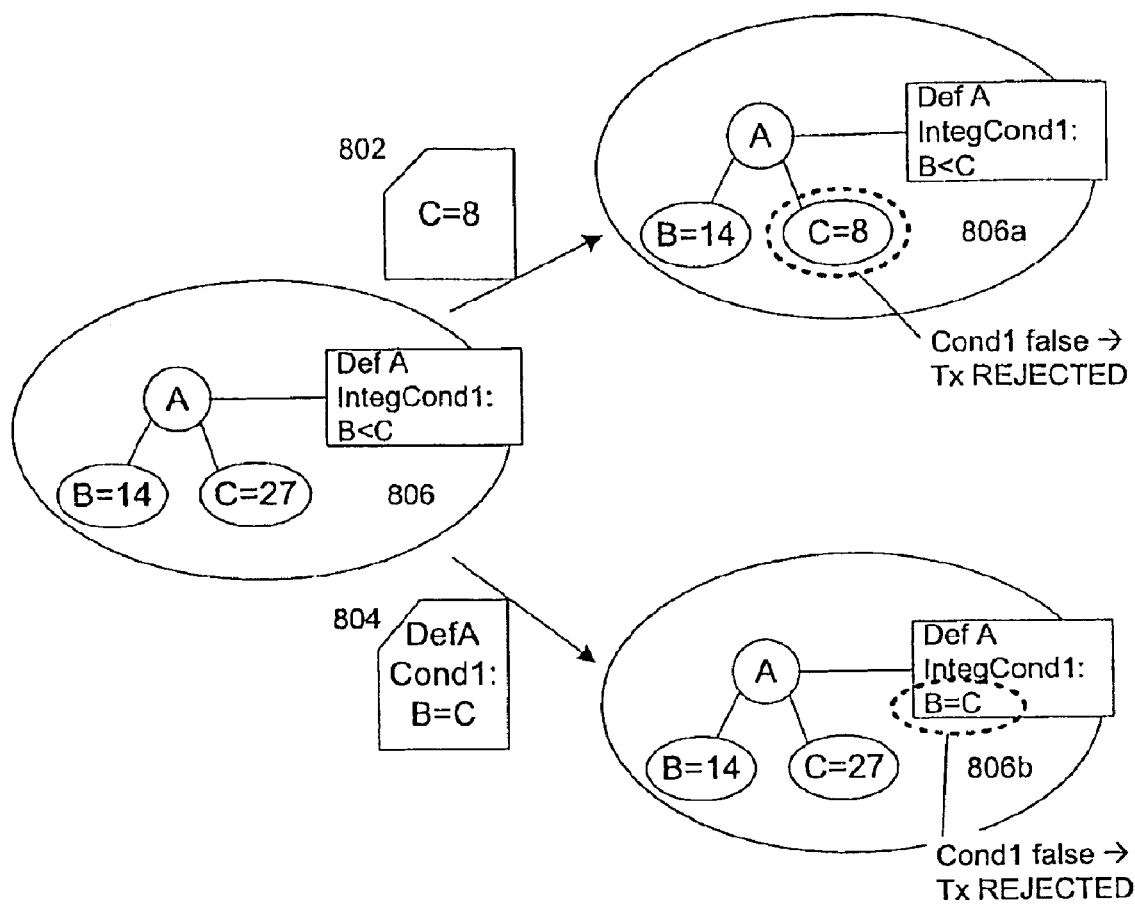
FIG. 8 is a block diagram of application of integrity conditions to transactions like that shown in FIG. 3.

For example, as shown in FIG. 8, a first transaction 802 changes the value of a data element C to create a version 806a of a model 806. This change violates an integrity condition 808 that element B must have a lower value than element C, hence the modification violates an existing rule, and the transaction 802 is rejected. On the other hand, a second transaction 804 modifies the existing integrity condition 808, replacing it with a condition 808a in a revised model 806b that requires that the value of element B be equal to that of element C. Since the data does not currently comply with that rule, the new integrity condition 808a would be violated and the transaction 804 adding it is rejected.

An integrity condition is attached to an element in the same manner as a permission. It contains an ID and a dynamic expression returning a Boolean. Unlike permissions, the dynamic expression is evaluated after any modification attempt is applied, and integrity conditions can use only the data model. They cannot use external information such as roles of users or the current date because integrity conditions are not relative to a specific transaction.

In some examples, there is a sub-category of integrity conditions called "preconditions." A precondition uses a dynamic expression whose evaluation doesn't require the data element on which the condition applies. For example, a precondition for a StudyEvent "FOLLOWUP" may be "existence of the StudyEvent "SCREENING." Evaluation of the expression doesn't use the data associated with the element "FOLLOWUP."

On the server side, preconditions are evaluated in the same manner as other integrity conditions. However, they are useful on the client side because they can be used by the user interface to show graphically if an item (or any data container) can be entered in the current context, before the user tries to type anything in their local interface, such as a clinical record form (CRF).

Hierarchy Conditions

In examples with hierarchical data, a condition (permission or integrity) can be linked to the data hierarchy in two ways. A condition may be linked to the containing definition where the condition is attached (or the data element at evaluation time), or it may be linked to a target path, which indicates to which data element the condition applies. The containing definition owns the condition. If a definition is deleted, all its conditions are deleted. The containing definition also determines the scope of the condition. The scope is the area of the data hierarchy that is available to the dynamic expression, i.e., the subset of the model within which the expression can read input values.

The target path indicates which data element is checked by the condition. In some examples, the data path can only point to a data element below the containing element in the data hierarchy. In simple cases, the target path is the "empty" path, which means that the element that is validated by the condition is the same as the element to which the condition is attached.

There are two main reasons to attach a condition at a higher level than the element it constrains. One is to add a constraint on shared definition, but only in a specific context. The other main reason is to widen the scope of the visible data to take "external" variables into account in the expression.

Figure 9:
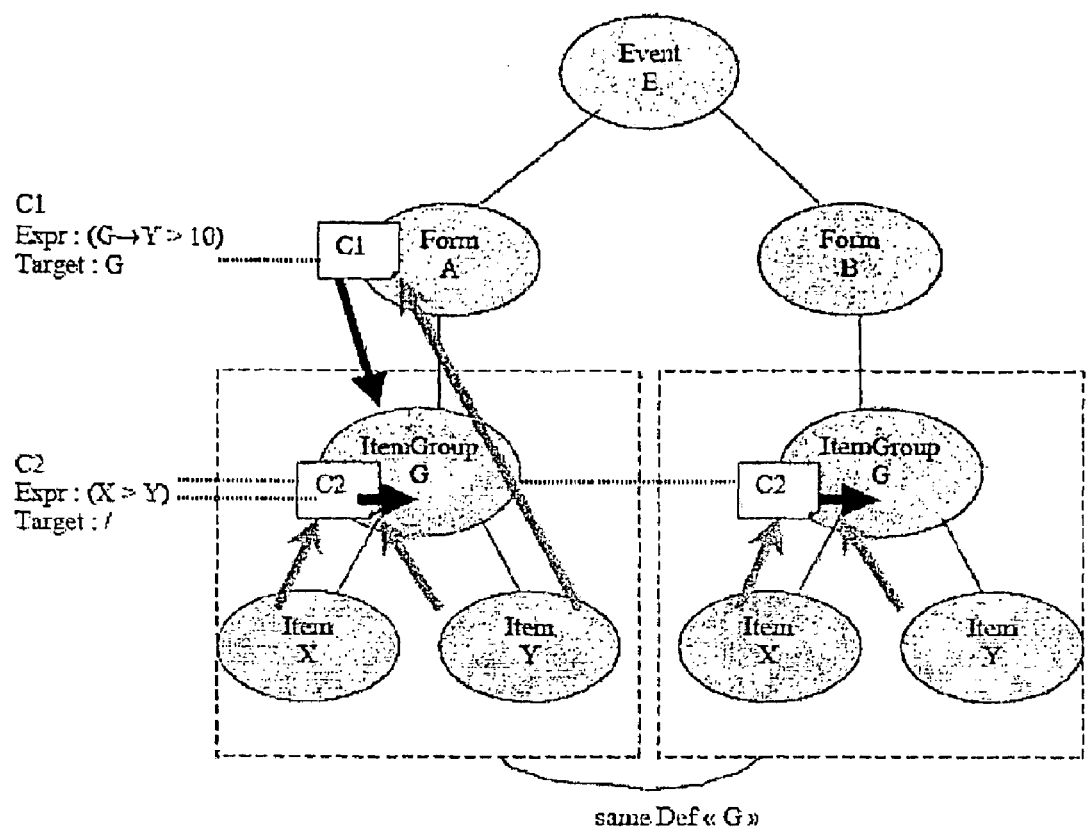
FIGS. 9-10 are block diagrams of rules in a hierarchical model like that shown in FIG. 2.

In the example of FIG. 9, item group G has the constraint "C2." Constraint C1 applies to item group G but is attached to the form A, so it adds a constraint on G only if G is contained in A, that is, the other item group G, in form B, is not affected by constraint C1.

Figure 10:
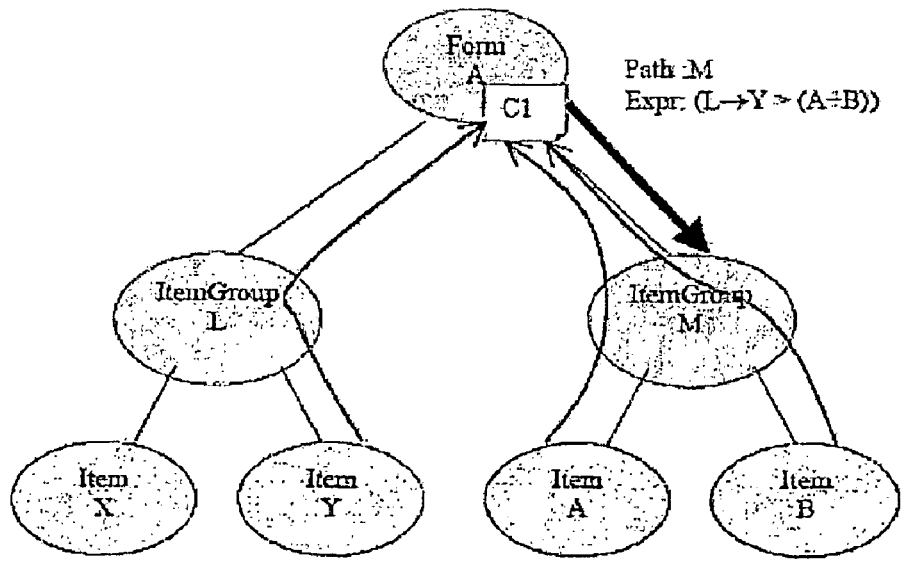

In the example of FIG. 10, constraint C1 applies to item group M, but since it must reference data from another item group (L), it is attached at a higher level. At form A, the scope is wide enough to access item Y in Item Group L and allow constraint C1 to be evaluated.

Expressions

An expression is an object which is able to perform some dynamic evaluation. It can have parameters and contain child sub-expressions. Parameters are values that are fixed during the system construction and cannot be dynamic (for example the number of decimals in a Round operation). In some examples, the expression attached to a condition is the root of a tree of nested expressions.

The expression assembly can be done at runtime by some users, but the expression types are fixed in the controller code. Expression types are the primitive blocks with which advanced expressions can be built. Sample expression types are: AND, OR, ADD, and SUBTRACT. While most expression types combine their input values to build the result (for instance AND), some expressions don't have any sub-expression and are the leaves of the evaluation tree. They read data (or constants), return contextual data, or test user roles.

Figure 11:
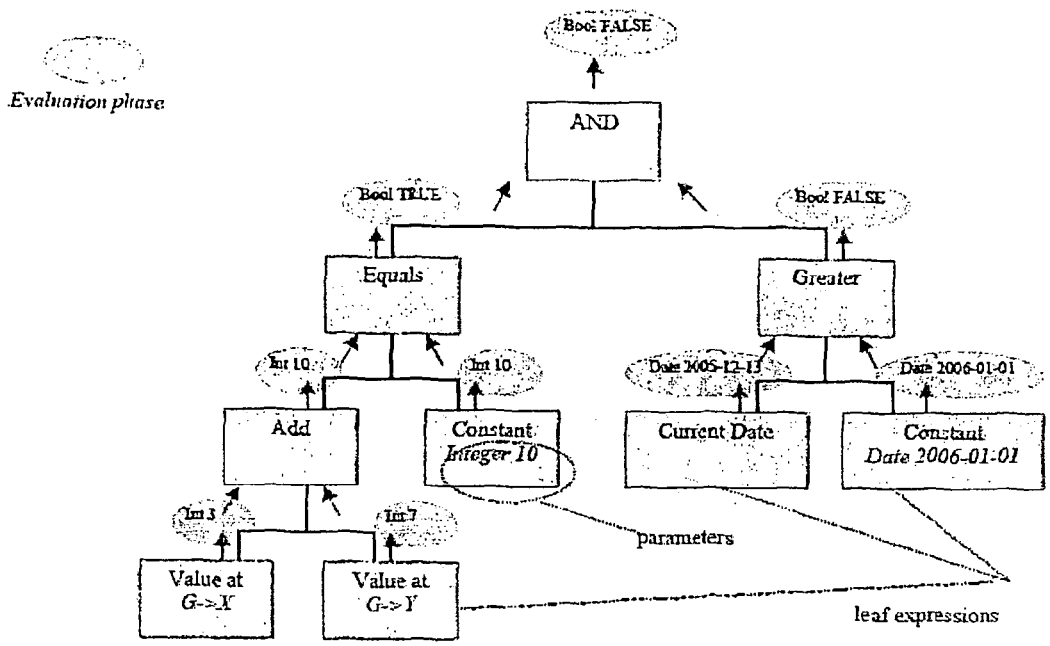
FIG. 11 is a block diagram of the evaluation of a rule like that shown in FIG. 9.

FIG. 11 shows a sample expression that can be attached to a form containing an item group "G" containing 2 items "X" and "Y" of type "Integer," such as form A in FIG. 9. During evaluation, an expression does not directly use its sub expressions, but uses only the results of the isolated evaluation of each sub expression, shown in ovals. Such intermediate results return values of the same type as the primitive values of DataItems in the CDISC data hierarchy, which makes the data model of CDISC and the dynamic expression system of K3 homogenous and consistent. For example, if an operation uses a value of type "date," the value object used is the exact representation of the date format defined for CDISC data items. This value does not have to be in the native date format that would be used in, for example, an Oracle SQL statement or the standard Date class defined in the Java language. This provides advantages because there may be differences between implementations, for example, the standard Java Date class includes hours, while the CDISC date includes only year, month, and day. This evaluation method allows an expression's validity to be checked at the time of its construction, for example, an AND expression cannot contain sub-expressions that return non-Boolean values. This provides advantages similar to those of a strongly-typed language because each computed value has a well-defined type, unlike scripting languages such as JavaScript or PHP.

Since expressions can use only fixed sources like clinical data, contextual date and time, or user roles, their evaluations are fully reproducible. Moreover, any evaluation of an expression cannot change the current state of the model (only transactions can do that). In other words, there cannot be "side-effects" during the evaluation. This provides a more robust solution and allows future optimization (e.g., the addition of a cache or parallel evaluation).

In some examples, expressions may also be used to define virtual data items that are not stored, but are computed with an expression each time they are read.

For instance, a virtual data item can be used to compute and display a patient's Body Mass Index (BMI). If the value for the mass or the height of the patient is changed, the BMI will automatically be updated. Such virtual data items can be referenced in expressions like normal data items.

Roles

An important aspect of the model in a clinical study is the role of each user. Often a user has several different roles and these roles don't apply to the same organization or geographical area. In some examples, users have roles only for specified structures. For instance, a user can have the "investigator" role in "Paris" and the "monitor" role in "France".

Figure 12:
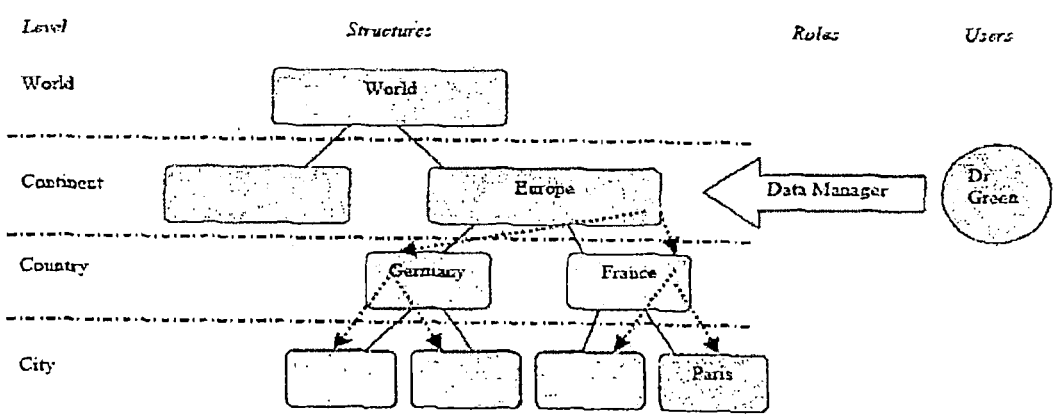
FIG. 12 is a block diagram of the inheritance of roles in a hierarchical model like that shown in FIG. 2.

As shown in the example of FIG. 12, the structures may be organized in a hierarchy. If a user has a role on a structure, then the same role is granted to him on all sub-structures. If a user has a role of "DataManager" in "Europe," he can use the same role in "Germany" and "France," and also all the cities of these countries.

A role can inherit attributes from one or several other roles. In addition, the inherited role can be promoted to a higher level in the structure hierarchy. For example, a role "invest-dm" can inherit from the role "investigator" at the same level and from the role "data manager" defined at the "country" level. This means that if a user is granted the "invest-dm" role in "Paris" (at the "city" level), then he automatically has the role "data manager" in the parent country, i.e., "France".

Each subject data element is linked to exactly one structure. In some examples, for business reasons, data elements are linked only to leaf structures, e.g., records for a patient are linked only to a hospital, not to a city or country structure that might contain hospitals. When a condition referencing a role is evaluated for a given data, then the system recovers the associated structure which determinates if the user has the given role in this context.

A number of embodiments of the invention have been described. Nevertheless, it will be understood that various modifications may be made without departing from the spirit and scope of the invention. For example, data formats and programming environments other than those described may be used. The techniques described may be used for managing data other than clinical data, for example, medical product quality control data. Accordingly, other embodiments are within the scope of the following claims.

What is claimed is:

1. A computer-implemented method of managing healthcare information data of a clinical trial, the method comprising:
   storing, in a short term storage component and a long term storage component, a data model that includes elements and associated values, the elements including clinical trial data, wherein the short term storage component maintains a representation of a current state of the data model;
   receiving, by a controller module, a transaction instructing a change to a first current state of the data model, wherein the transaction includes an instruction to add, remove, or change values of elements of the data model, or an instruction to change relationships between elements of the data model;
   analyzing the change instructed by the transaction;
   making a backup copy of a portion of the data model that is to be modified by the transaction;
   generating a revised data model by implementing the received transaction and storing the revised data model in the short term storage component as a new current state;
   checking the new current state against a set of rules to determine whether the revised data model violates a rule among the set of rules;
   if a rule among the set of rules is violated, rejecting the transaction and using the backup copy to restore the data model in the short term storage component to the first current state; and
   if a rule among the set of rules is not violated, storing the transaction in the long term storage component.

2. The method of claim 1 in which generating a revised data model comprises altering a rule in the data model.

3. The method of claim 2 in which checking the new current state against a set of rules to determine whether the revised data model violates a rule among the set of rules comprises evaluating the new current state of the data model.

4. The method of claim 3 in which checking the new current state against a set of rules to determine whether the revised data model violates a rule among the set of rules comprises
   evaluating a dynamic expression including a set of operations identifying a type of modification to the first current state of the data model and an ID and wherein the dynamic expression is unique to an element to which it is attached; and
   determining that the transaction represents the modification to the data model matching the type identified by the ID attached to the element.

5. The method of claim 4 in which evaluating the dynamic expression comprises
   determining a relationship between a user submitting the transaction and a set of users.

6. The method of claim 5 in which the relationship is that the user is a member of the set of users.

7. The method of claim 5 in which
   the relationship is that the user is a member of a first set of users, and the relationship is satisfied if the user is a member of a second set of users that is related to the first set of users.

8. The method of claim 2 in which the new current state is checked against the set of rules after each attempt to modify the data model.

9. The method of claim 8 in which checking the new current state against a set of rules to determine whether the revised data model violates a rule among the set of rules comprises
   evaluating a dynamic expression including a set of operations identifying a type of modification to the first current state of the data model and an ID and wherein the dynamic expression is unique to an element to which it is attached; and
   determining that the transaction represents the modification to the data model matching the type identified by the ID attached to the element.

10. The method of claim 4 in which evaluating the dynamic expression comprises determining a relationship between two or more of:
    a value of an element in the model,
    a value of an item of data external to the model,
    a value of an element in the transaction, and
    a result of a computation.

11. The method of claim 1 in which checking the new current state against a set of rules to determine whether the revised data model violates a rule among the set of rules comprises evaluating an expression.

12. The method of claim 11 in which the expression comprises sub-expressions, and evaluating the expression comprises evaluating each of the sub-expressions to produce results, and evaluating the expression based on the results.

13. The method of claim 11 in which the expression includes a definition of a data item, and evaluating the expression includes constructing the data item according to the definition.

14. The method of claim 1 wherein checking the new current state against a set of rules to determine whether the revised data model violates a rule among the set of rules comprises identifying a hierarchy of elements, wherein a rule among the set of rules is associated with a first element in the hierarchy, determining that a second element is subordinate to the first element and evaluating the value of the second element.

15. The method of claim 14 in which the second element is a child of the first element.

16. The method of claim 1 wherein checking the new current state against a set of rules to determine whether the revised data model violates a rule among the set of rules comprises identifying a hierarchy of elements, wherein a rule among the set of rules is associated with a first element in the hierarchy, and evaluating values of a second and third element that are each subordinate to the first element but not to each other.

17. The method of claim 16 in which at least one of the second and third elements is a child of the first element.

18. An apparatus for managing healthcare information data of a clinical trial, the apparatus comprising a computer configured to:
   store, in a short term storage component and a long term storage component, a data model that includes elements and associated values, the elements including clinical trial data, wherein the short term storage component maintains a representation of a current state of the data model;
   receive, by a controller module, a transaction instructing a change to a first current state of the data model, wherein the transaction includes an instruction to add, remove, or change values of elements of the data model, or an instruction to change relationships between elements of the data model;
   analyze the change instructed by the transaction;
   make a backup copy of a portion of the data model that is to be modified by the transaction;
   generate a revised data model by implementing the received transaction and store the revised data model in the short term storage component as a new current state;
   check the new current state against a set of rules to determine whether the revised data model violates a rule among the set of rules;
   if a rule among the set of rules is violated, reject the transaction and use the backup copy to restore the data model in the short term storage component to the first current state; and
   if a rule among the set of rules is not violated, store the transaction in the long term storage component.

19. The apparatus of claim 18 in which the computer is configured to maintain the data model by, for each transaction in a set of transactions,
   if the transaction alters data in the first current state of the data model, altering corresponding data in the new current state,
   if the transaction alters a rule in the first current state of the data model, altering a corresponding rule in the new current state.

20. The apparatus of claim 19 in which the computer is configured to evaluate the new current state of the data model.

21. The apparatus of claim 20 in which the computer is configured to
   evaluate a dynamic expression including a set of operations identifying a type of modification to the first current state of the data model and an ID and wherein the dynamic expression is unique to an element to which it is attached; and
   determine that the transaction represents the modification to the data model matching the type identified by the ID attached to the element.

22. The apparatus of claim 21 in which the computer is configured to check the new current state against the set of rules after each attempt to modify the data model.

23. A non-transitory computer readable medium for managing healthcare information data of a clinical trial, the medium comprising instructions to cause a computer to
   store, in a short term storage component and a long term storage component, a data model that includes elements and associated values, the elements including clinical trial data, wherein the short term storage component maintains a representation of a current state of the data model;
   receive, by a controller module, a transaction instructing a change to a first current state of the data model, wherein the transaction includes an instruction to add, remove, or change values of elements of the data model, or an instruction to change relationships between elements of the data model;
   analyze the change instructed by the transaction;
   make a backup copy of a portion of the data model that is to be modified by the transaction;
   generate a revised data model by implementing the received transaction and store the revised data model in the short term storage component as a new current state;
   check the new current state against a set of rules to determine whether the revised data model violates a rule among the set of rules;
   if a rule among the set of rules is violated, reject the transaction and use the backup copy to restore the data model in the short term storage component to the first current state; and
   if a rule among the set of rules is not violated, store the transaction in the long term storage component.

24. The medium of claim 23 in which the instructions also cause the computer to maintain the data model by, for each transaction in a set of transactions,
   if the transaction alters data in the first current state of the data model, altering corresponding data in the new current state,
   if the transaction alters a rule in the first current state of the data model, altering a corresponding rule in the new current state.

25. The medium of claim 24 in which the instructions also cause the computer to evaluate the new current state of the data model.

26. The medium of claim 25 in which the instructions also cause the computer to
   evaluate a dynamic expression including a set of operations identifying a type of modification to the first current state of the data model and an ID and wherein the dynamic expression is unique to an element to which it is attached; and
   determine that the transaction represents the modification to the data model matching the type identified by the ID attached to the element.

27. The medium of claim 23 in which the instructions cause the computer to check the new current state against the set of rules after each attempt to modify the data model.

* * * * *